(12) United States Patent
Peterson et al.

(10) Patent No.: US 6,755,857 B2
(45) Date of Patent: Jun. 29, 2004

(54) POLYMER HEART VALVE WITH PERFORATED STENT AND SEWING CUFF

(75) Inventors: Paul C. Peterson, Austin, TX (US); Riyad Moe, Austin, TX (US); Joseph A. Chinn, Austin, TX (US)

(73) Assignee: Sulzer Carbomedics Inc., Austin, TX (US)

( * ) Notice: Subject to any disclaimer, the term of this patent is extended or adjusted under 35 U.S.C. 154(b) by 56 days.

(21) Appl. No.: 10/020,337

(22) Filed: Dec. 12, 2001

(65) Prior Publication Data

US 2003/0109922 A1 Jun. 12, 2003

(51) Int. Cl.[7] .................................................. A61F 2/06
(52) U.S. Cl. ....................... 623/2.17; 623/2.19; 623/900
(58) Field of Search ................................. 623/2.1, 2.12, 623/2.17–2.19, 2.38, 2.4, 900, 11.11, 66.1, 2.41, 2.42

(56) References Cited

U.S. PATENT DOCUMENTS

| | | | |
|---|---|---|---|
| 3,739,402 A | * 6/1973 | Cooley et al. ............. 623/2.16 |
| 4,084,268 A | 4/1978 | Ionescu et al. ................. 3/1.5 |
| 4,345,340 A | 8/1982 | Rosen ............................ 3/1.5 |
| 4,364,126 A | 12/1982 | Rosen ............................ 3/1.5 |
| 4,364,127 A | 12/1982 | Pierce et al. ................... 3/1.5 |
| 4,501,030 A | 2/1985 | Lane .............................. 3/1.5 |
| 4,626,255 A | 12/1986 | Reichart et al. ............... 623/2 |
| 4,680,031 A | 7/1987 | Alonso .......................... 623/2 |
| 4,816,029 A | 3/1989 | Penny, III et al. ............. 623/2 |
| 5,147,391 A | * 9/1992 | Lane .......................... 623/2.18 |
| 5,258,023 A | 11/1993 | Reger ............................ 623/2 |
| 5,411,552 A | * 5/1995 | Andersen et al. .......... 623/2.18 |
| 5,562,729 A | 10/1996 | Purdy et al. ................... 623/2 |
| 5,755,782 A | 5/1998 | Love et al. .................... 623/2 |

FOREIGN PATENT DOCUMENTS

| WO | WO 00/23006 | 4/2000 | |
|---|---|---|---|
| WO | WO 00/23006 A1 | * 4/2000 | ............. A61F/2/24 |

* cited by examiner

Primary Examiner—David J. Isabella
Assistant Examiner—Umi Chattopadhyay
(74) Attorney, Agent, or Firm—Williams, Morgan and Amerson

(57) ABSTRACT

A prosthetic heart valve having an elastomeric stent with an annular base and a plurality of apertures or holes circumferentially spaced around the base for receiving a suture. Flexible polymeric leaflets are molded over the stent. Polymeric material surrounds the apertures, leaving a central opening in each aperture. The base may be a frustro-conical ring. A sewing ring is mounted on the heart valve by suturing the ring through the apertures. Apertures or holes may also be provided by extending an area covered by woven material around all or part of the circumference of the base.

26 Claims, 3 Drawing Sheets

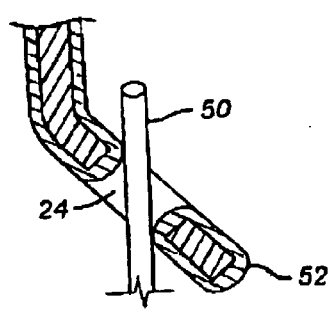
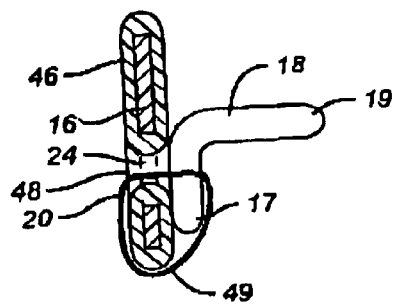
FIG. 7          FIG. 9
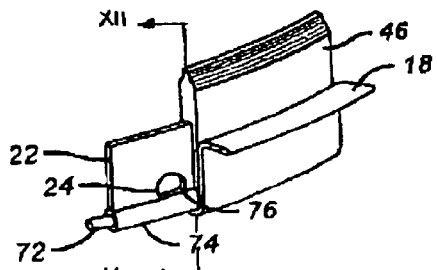
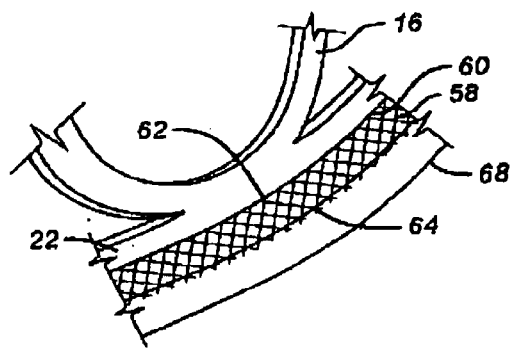
FIG. 12          FIG. 14
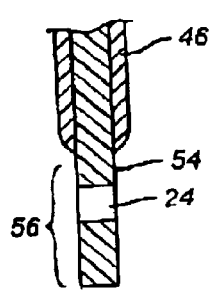
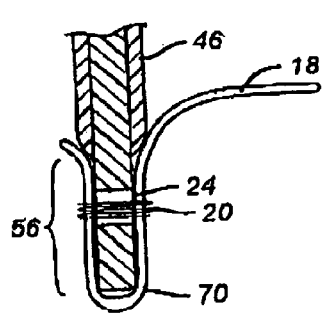
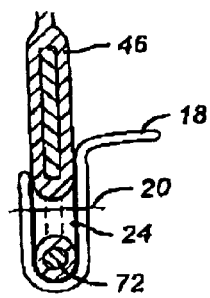
FIG. 10      FIG. 11      FIG. 13

POLYMER HEART VALVE WITH PERFORATED STENT AND SEWING CUFF

BACKGROUND

TECHNICAL FIELD

The present invention pertains to prosthetic heart valves and in particular to polymeric tri-leaflet heart valve prostheses.

BACKGROUND OF THE INVENTION

Ever since 1950, when blood oxygenators made open heart surgery feasible, it has been possible to treat some forms of heart disease by replacing a patient's heart valve with a prosthetic valve. A prosthetic heart valve is implanted into an annular opening in a heart created when the diseased valve is removed. Early heart valve prostheses included ball-and-cage valves and disc-and-cage valves in which a ball or a disc was housed in a cage. One side of the cage provided an orifice through which blood flowed either into or out of the heart, depending on the valve being replaced. When blood flowed in a forward direction, the energy of the blood flow forced the ball or disc to the back of the cage allowing blood to flow through the valve. When blood attempted to flow in a reverse direction, or "regurgitate," the energy of the blood flow forced the ball or disc into the orifice in the valve and blocked the flow of blood.

A "mechanical" valve is another type of prosthesis comprising an annular valve body in which one, two, or three occluders are pivotally mounted. The occluders are typically substantially rigid. The occluders move between a closed position, in which the occluders are mated and block blood flow in the reverse direction, and an open position, in which the occluders pivot away from each other and do not block blood flow in the forward direction. The energy of blood flow causes the occluders to move between their open and closed positions.

The valve leaflets of "tissue valves" are usually flexible and made from tissue, such as specially treated porcine or bovine pericardial tissue. A tri-leaflet tissue valve comprises an annular valve body in which three flexible leaflets are mounted to a supporting portion of the valve body, called a "stent," located at the circumference of the annulus. When blood flows in the forward direction, the energy of the blood flow deflects the three leaflets away from the center of the annulus and allows blood to flow through. When blood flows in the reverse direction, the three leaflets engage each other in a coaptive region, occlude the valve body annulus and prevent the flow of blood.

Heart valves made from a man-made material such as polyurethane or another biocompatible polymer may have two or three leaflets and may have a stent to increase the structural strength of the valve while allowing the leaflets to remain flexible. Polymeric valves may be sutured or pinned directly to the site of an explanted heart valve, or a sewing ring may be sutured to the valve body and sutures attaching the valve to the heart may pass through the sewing ring. In either case, suturing through a polymeric valve body is likely to alter or damage the polymeric material where a suturing needle is driven through the valve body. High stresses and stress concentrations at suture locations may damage the valve body material.

An important consideration in prosthetic heart valve design is the durability of the heart valve. One source of failure of polymeric heart valves is tearing of the polymeric material that forms the heart valve, for example, where a suture needle has been driven through elastic polymeric material.

SUMMARY OF THE INVENTION

The invention improves the durability of elastic polymeric heart valves by eliminating the need to pierce the elastic material of the heart valve during construction of the sewing ring or during implantation. The prosthetic heart valve comprises a stent with an annular base and a plurality of commissures rising from the base. A plurality of apertures or holes circumferentially spaced around the circumference of the base provide access points for a needle to draw a suture through the aperture. Flexible polymeric leaflets are cast or molded over the stent. Polymeric material forming the leaflets covers most of the stent, including at least part of the base. The polymeric material may surround the apertures or holes, leaving a central opening in each aperture through which the needle may be inserted without penetrating the polymeric material. Alternatively, only a portion of the base may be covered with polymeric material, such that the polymeric material does not extend to the apertures. In this configuration the needle can pass through an aperture without penetrating the polymeric material. The base may be flared outwardly, forming a frustro-conical ring, to facilitate formation of the central openings in each aperture when the polymeric material is molded over the stent.

A sewing ring may be mounted on the heart valve by suturing the sewing ring through the apertures in the stent. The sewing ring may be attached outside the base or inside of the base, if the base is flared outwardly.

The apertures or holes may have a variety of configurations, such as circular or elongated slots. The apertures may be formed as a plurality of notches along an edge of the base of the stent with a circumferential wire lying along the edge of the base and closing an open side of the notches.

Apertures may also be provided by extending an area covered by woven material around all or part of the circumference of the base.

It is an object, therefore, of the present invention to provide a polymeric prosthetic heart valve with means for attaching a sewing cuff or for suturing directly to the heart without puncturing a polymeric material.

It is another object of this invention to provide a polymeric prosthetic heart valve wherein the structural integrity of the valve material is not compromised by punctures during manufacture.

Yet another object of the invention is to provide a polymeric, stent-supported heart valve body having preformed apertures for attaching a sewing ring.

These and other objects and features of the invention will be apparent from the following detailed description, made with reference to the accompanying drawings.

BRIEF DESCRIPTION OF DRAWINGS

FIG. 7 is the view of FIG. 6 with a molding pin inserted through an aperture in the stent.

FIG. 9 is a partial through section of a portion of a heart valve illustrating attachment of a sewing ring.

FIG. 10 is a through section similar to FIG. 6, illustrating a partially enclosed stent.

FIG. 11 is the view of Fig. 10, further illustrating an attached sewing ring.

FIG. 12 is a view of a portion of a further embodiment of a stent for use in a polymer heart valve.

FIG. 13 is a through section view of the stent of FIG. 12 at line XII—XII, further illustrating an attached sewing ring.

FIG. 14 is a view of a section of a circumferential woven, bias ply band attached to a section of the lower edge of the base of a stent.

DESCRIPTION OF THE PREFERRED EMBODIMENTS

Figure 1:
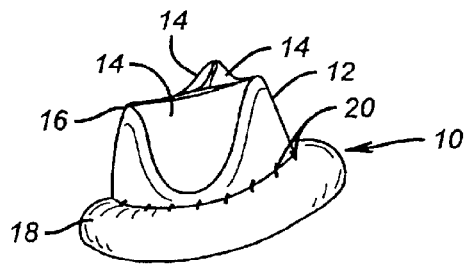
FIG. 1 is a perspective view of a polymer heart valve.

A tri-leaflet heart valve 10 comprises an annular elastic valve body 12 and three flexible leaflets 14 made of a biocompatible polymer such as silicone or polyurethane, as shown in FIG. 1. A stent 16, made of metal or plastic, reinforces the elastic valve body. The stent 16 is at least partially embedded in the elastic material that forms the valve body 12, as shown in FIG. 1. A sewing ring 18 circumscribes the valve body 12. The sewing ring is attached to the valve body by pins or sutures 20. The pins or sutures pass through apertures in the stent and elastic material as described below. The valve 10 may also omit the sewing ring 18.

In some prior art polymer heart valve designs without a sewing ring, sutures or pins were placed through an outside edge of the valve body 12 for attachment of the valve to the host tissue. When sewing rings were used, sutures 20 or pins placed through the outside edge of the valve body held the sewing ring to the valve body. In either case, the needle holes in the valve body 12 through which the sutures 20 or pins pass are locations for crack initiation. Such propagation will lead to incompetence of the leaflet and eventual structural failure of the leaflet 14. A heart valve according to the present invention provides suture or attachment apertures which are preformed such that polymeric material of the valve is not punctured either during the process of attaching a sewing ring to the valve or during implantation in the heart. Cracks or stress concentrations are therefore less likely to develop.

Figure 2:
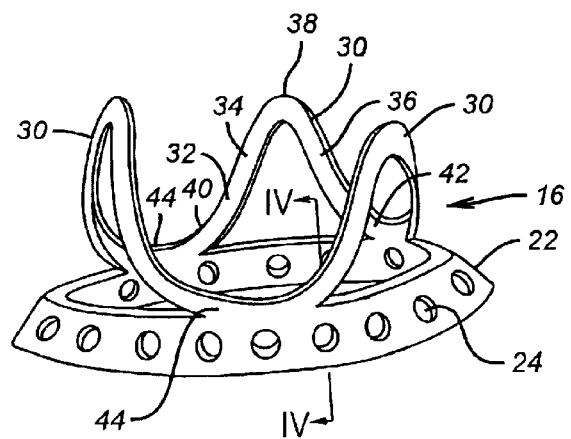
FIG. 2 is a perspective view of a stent for a polymeric heart valve.
Figure 3:
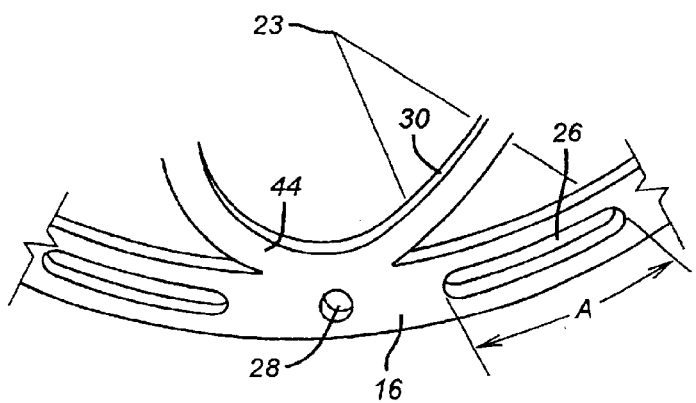
FIG. 3 is a perspective view of a portion of further embodiment of the stent of FIG. 2.

In FIG. 2, the stent 16 has a circumferential base 22. The base may be generally ring-like in configuration or it may be scalloped to conform to the anatomy common at sites of explanted natural valves. A plurality of apertures or holes 24 spaced circumferentially around the base provides openings for sutures, pins, or other attachment apparatus, as explained below. The apertures 24 may have any suitable shape, such as round, elliptical or elongated. As shown in FIG. 3, elongated apertures or slots 26 subtend a predetermined angle A having a vertex 23 near the geometric center of the circumferential base 22. For three slots, the angle A would be less than 120°. For six slots, the angle A would be less than 60°. Sutures can be threaded through the slots 26 and the valve may be rotated into a slightly more favorable orientation. Other round apertures 28 may be used to secure the valve in a final position.

A plurality of commissure supports 30 rise from the base 22 and define a generally cylindrical area for the leaflets 14. A bi-leaflet valve would have two commissure supports. A tri-leaflet valve would have three commissure supports, as shown in FIG. 2. More leaflets and commissures are possible, but are generally not justified because of increased complexity. In the preferred embodiment, a commissure support 30 comprises a ribbon-like segment of polymeric or other material formed into two opposed concave legs 34, 36. The legs 34, 36 are flared apart near the base 22. Distally from the base 22, the legs 34, 36 approach each other and are joined by a convex apex segment. Each leg 34, 36 is joined to the base 22 at a proximal end 40, 42. Preferably the commissure supports 30 taken together form a smooth, closed curve circumferentially around the base 22. The apex segments 38 usually form tighter curves than a curve 44 between two adjacent commissure supports. Those of skill in the art will recognize that other configurations and materials, such as wire, for example, may be used for commissure supports.

Figure 4:
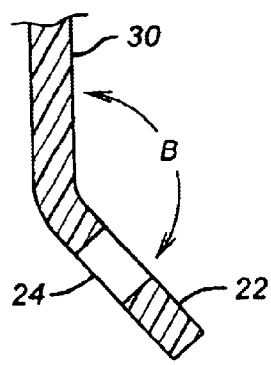
FIG. 4 is a through section of a portion of the stent of FIG. 2, taken at line IV—IV.

In certain embodiments, the base 22 may be flared outwardly away from the commissure supports, as shown in FIG. 2. The base has a frustro-conical shape and forms an angle B as shown in FIG. 4 between the commissure supports 30 and the base 22. The angle B is preferably between about 90° and about 130°. This angle helps in manufacturing certain configurations of heart valves, as will be explained hereafter. In certain configurations, the base may be cylindrical, as shown in FIGS. 10 through 13.

Figure 5:
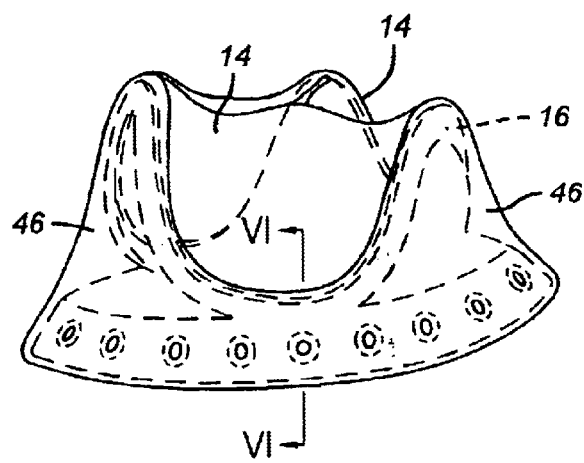
FIG. 5 is a perspective view of the stent of FIG. 2 with elastomeric polymer leaflets molded thereon.
Figure 6:
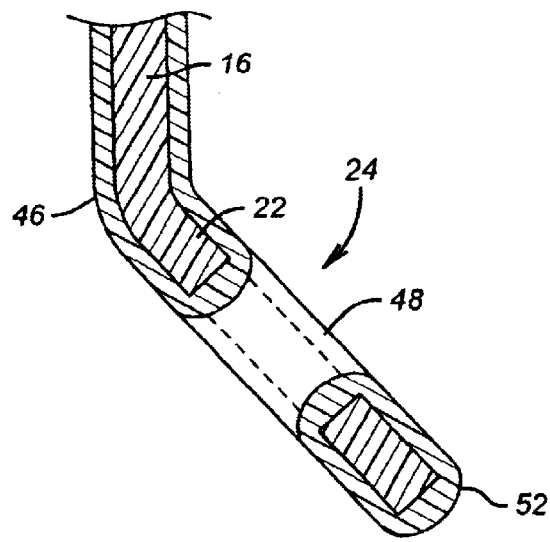
FIG. 6 is a through section of a portion of the stent and leaflets of FIG. 5 taken at line VI—VI.

The stent 16 may be placed in a mold and encased in a flexible polymeric material 46, as shown in FIG. 5. The flexible polymer material is simultaneously formed into leaflets 14. At the apertures 24 in the base 22, the polymeric material 46 is formed over the stent 16 in such a manner as to leave an opening 48 though the aperture 24. This may be done, for instance, by inserting a pin 50 through the aperture 24 as shown in FIG. 7. The pin 50 is supported by a mold (not shown) such that polymeric material can be injected around the stent 16. After the polymeric material has set, the mold is removed. As a consequence of the flare of the base 22, defined by the angle B, the pins 50 can be more easily withdrawn from the apertures 24, leaving the openings 48 clear to receive a suture or fastener.

Figure 8:
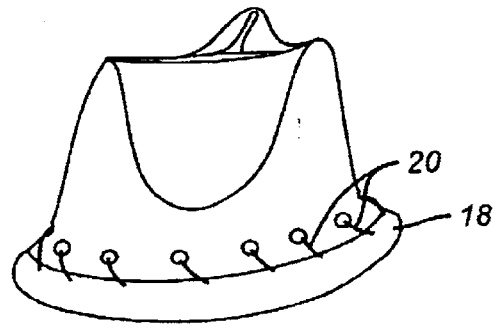
FIG. 8 is a perspective view of a polymeric heart valve with stent and leaflets as shown in FIG. 5 and attached sewing cuff.

In certain embodiments, the sewing ring 18 can be placed below and slightly inside the base 22, as shown in FIG. 8. This configuration would allow the heart valve to have a somewhat larger central orifice when compared with the configuration of FIG. 1, for example. Optimizing the orifice size decreases resistance to blood flow through the valve. To attach the sewing ring, the suture 20 could be inserted through the opening in an aperture towards the inside of the valve, then passed down under a lower edge 52 of the valve and brought out through the sewing ring.

In FIG. 9, another way of attaching the sewing ring to either a straight base (as expressly shown in FIG. 9) or a canted or flared base such as FIG. 7. The sewing ring 18 is placed against the outside of the valve body and sutures 20 or other fasteners are passed through the openings 48 in the apertures 24. The sutures are passed first through the valve body and then through the sewing ring. The sutures are then passed beneath a down stream edge 49 of the valve body and again through the valve body and sewing ring. The sutures or fasteners attach a secured end 17 of the sewing ring to the annular valve body. A free end 19 of the sewing ring extends radially outwardly, forming and area that can receive sutures to attach the valve to cardiac tissue.

A series of suture apertures or holes free from polymeric material may also be provided by only partially covering the base with polymeric material. As illustrated in FIG. 10, the polymeric material 46 would extend only to a midpoint 54 of the base, leaving an exposed region 56. The apertures 24 would be in the exposed region 56, and thus the polymeric material would not be compromised. Care should be taken to insure a satisfactory bond between the polymeric material and the stent. Campbell and Moe have suggested partially exposing a linear portion of a stent in commonly assigned U.S. application Ser. No. 09/174,387, incorporated herein in its entirety by this reference. As shown in FIG. 11, the sewing ring 18 can have an attachment portion 70 folded to contact both the inside and outside surfaces of the exposed region 56. The suture 20 is passed through the apertures 24 and through the attachment portion on both the inside of the attachment portion and the outside of the attachment portion. Since the polymeric material 46 does not reach the apertures, the structural integrity of the polymeric material is not compromised by a needle drawing the suture through the apertures 24 or by another fastener inserted through the apertures.

The embodiment of FIG. 12 and FIG. 13 is similar to the embodiment of FIG. 10 and FIG. 11 in that it has an aperture in the base 22 of the stent, and at least a portion of the stent is embedded in the polymeric material 46. The embodiment of FIG. 12 and FIG. 13 has a wire 72 cast into the base 22 of the stent 16 at an upstream edge 74. In FIG. 12 and FIG. 13 the entire stent is coated with polymeric material 46 in such a manner as to leave an opening through the aperture 24 and the sewing ring 18 is attached by passing the suture 20 through the apertures 24. The imbedded wire 72 gives additional strength to the base to resist forces acting on the valve in the downstream direction, that is, in the direction of forward blood flow through the valve. Because of this added strength, the apertures 24 can be placed off-center on the base 22. With the apertures closed to the upstream edge 74, more of the material in the base 22 can resist forces acting on the valve in the upstream direction, that is when the valve closes. Consequently, the overall height of the base can be reduced. The apertures may be formed as a plurality of notches 76 along the upstream edge 74 of the base of the stent with the circumferential wire 72 lying along the upstream edge 74 of the base and closing an open side of the notches. The sewing ring 18 can be attached either from the outside, as in FIG. 9, by folding an attachment portion on both the inside and the outside of the base 22, as shown in FIG. 13, or from the inside, as shown in FIG. 8. The base 22 may be canted outwardly to form a frustro-conical ring, as described above in connection with FIG. 2.

A further embodiment illustrated in FIG. 14 employs a circumferential woven, bias ply band 58. An upper end 60 of the band 58 is cast into or affixed to a lower edge 62 of the base 22 of the stent 16. A lower end 64 of the band 58 is similarly cast into or affixed to an upper edge of a second base ring 68. The second base ring 68 distributes the forces exerted by the sutures on the band 58 and prevents the lower end 64 of the band from fraying and allowing the sutures to tear out of the band. The stent 16 including the base 22 is cast or molded into polymeric material forming the leaflets, but the polymeric material extends only to the upper end 60 of the band 58 or only slightly into the band 58, leaving most of the band and the second base ring exposed. Sutures may then be passed through the band 58 and a sewing ring in the manner shown in FIG. 9.

The foregoing describes preferred embodiments of the invention and is given by way of example only. For example, the invention is not limited to the manufacturing techniques disclosed but includes any manufacturing technique that leaves a portion of the stent outside the elastic material of the valve body. Further, the invention includes any prosthetic valve in which the prosthetic valve can be implanted without sutures or pins or the like piercing the elastic material of the valve body. The invention is not limited to any of the specific features described herein, but includes all variations thereof within the scope of the appended claims.

What is claimed is:

1. A prosthetic heart valve having an inside and an outside and comprising:
   a polymeric valve body having at least one leaflet, said leaflet having an open position and a closed position,
   a stent coupled to said valve body, said stent having a plurality of apertures, said apertures providing openings between the outside of the prosthetic heart valve and the inside of the prosthetic heart valve and said apertures being capable of receiving sewing ring fasteners, wherein said stent comprises a circumferential base and the apertures penetrate said base, wherein at least a portion of the stent is embedded in the polymeric valve body, and wherein said polymeric valve body encloses said base and includes a plurality of apertures in said polymeric valve body corresponding to said apertures in said base.

2. The prosthetic heart valve of claim 1 wherein said stent comprises a plurality of commissures in generally cylindrical configuration and said base is connected to said commissures at an upstream location and said base slants radially outwardly from said commissures.

3. The prosthetic heart valve of claim 2 wherein a junction between said commissures and said base forms an angle of between 90° and 135°.

4. The prosthetic heart valve of claim 1 further comprising a sewing ring circumferentially surrounding the base.

5. The prosthetic heart valve of claim 4 wherein said sewing ring is connected to said base at an upstream, inner side of said base.

6. The prosthetic heart valve of claim 1 wherein at least some of said apertures are slots.

7. The prosthetic heart valve of claim 6 wherein at least one of said apertures is generally circular.

8. The prosthetic heart valve of claim 1 further comprising a sewing ring circumferentially surrounding the valve body and the stent and attached to the stent by sewing ring fasteners extended through said apertures in said stent.

9. The prosthetic heart valve of claim 8 wherein the sewing ring fasteners are sutures.

10. The prosthetic heart valve of claim 1, wherein said stent further comprises an upstream edge and a wire connected to said edge wherein the apertures are downstream from said wire.

11. The prosthetic heart valve of claim 10 further comprising a sewing ring circumferentially surrounding the valve body and the stent and attached to the stent by sewing ring fasteners extended through said apertures in said stent.

12. The prosthetic heart valve of claim 11 wherein the sewing ring fasteners are sutures.

13. A prosthetic heart valve comprising:
   a polymeric valve body having at least one leaflet, said leaflet having an open position and a closed position,
   a stent molded within said valve body, said stent having a plurality of apertures, said apertures being exposed through said polymeric valve body.

14. The prosthetic heart valve of claim 13 wherein said stent comprises a circumferential base and wherein said apertures penetrate said base.

15. The prosthetic heart valve of claim 14 wherein said polymeric valve body encloses said base and includes a plurality of apertures in said polymeric valve body corresponding to said apertures in said base.

16. The prosthetic heart valve of claim 14 wherein said stent comprises a plurality of commissures in generally cylindrical configuration and said base is connected to said commissures at an upstream location and said base slants radially outwardly from said commissures.

17. The prosthetic heart valve of claim 16 wherein a junction between said commissures and said base forms an angle of between 90° and 135°.

18. The prosthetic heart valve of claim 14 further comprising a sewing ring circumferentially surrounding the valve body.

19. The prosthetic heart valve of claim 18 wherein said sewing ring is connected to said base at an upstream, inner side of said base.

20. The prosthetic heart valve of claim 14 wherein at least some of said apertures are slots.

21. The prosthetic heart valve of claim 20 wherein at least one of said apertures is generally circular.

22. The prosthetic heart valve of claim 13 further comprising a sewing ring circumferentially surrounding the valve body and the stent and attached to the stent by fasteners extended through said apertures in said stent.

23. The prosthetic heart valve of claim 22 wherein the fasteners are sutures.

24. The prosthetic heart valve of claim 13 wherein said stent further comprises an upstream edge adjacent blood flowing into the valve and a wire connected to said upstream edge wherein the apertures are downstream from said wire.

25. The prosthetic heart valve of claim 24 further comprising a sewing ring circumferentially surrounding the valve body and the stent and attached to the stent by fasteners extended through said apertures in said stent.

26. The prosthetic heart valve of claim 25 wherein the fasteners are sutures.

* * * * *